United States Patent [19]

Yamada

[11] Patent Number: 4,944,751
[45] Date of Patent: Jul. 31, 1990

[54] MATTED (DELUSTERED) ARTIFICIAL HAIR AND METHOD OF PREPARATION THEREOF

[76] Inventor: Shiro Yamada, No.2-7-1-606, Mita, Minato-ku, Tokyo, Japan

[21] Appl. No.: 301,861

[22] Filed: Jan. 4, 1989

Related U.S. Application Data

[62] Division of Ser. No. 183,224, Apr. 19, 1988, Pat. No. 4,880,428.

[30] Foreign Application Priority Data

Dec. 25, 1986 [JP] Japan .................... 61-307867

[51] Int. Cl.⁵ .............................................. A61F 2/10
[52] U.S. Cl. .......................................... 623/15; 28/219
[58] Field of Search ............... 623/15; 132/53; 28/219

[56] References Cited

U.S. PATENT DOCUMENTS 1,957,508 5/1934 Taylor ...................... 28/219

Primary Examiner—Randall L. Green
Assistant Examiner—Stephanie Iantorno
Attorney, Agent, or Firm—Browdy and Neimark

[57] ABSTRACT

A matted (delustered) artificial hair which is disclosed herein comprises a fiber made of a synthetic resin. A large number of irregular scrubbed flaws is formed circumferentially on the surface of a monofilament having a substantially circular section. A method for preparation of such an artifical hair which method comprises placing a bundle of monofilaments of a synthetic fiber and each having a substantially circular section between two abrasive-coated plates each having a soft layer on a surface thereof, and allowing the two abrasive-coated plates to reciprocate in the opposite directions at an angle of 45° to 90° with respect to the longitudinal direction of the monofilament while applying a slight pressure in the presence of an abrasive, whereby a large number of scrubbed flaws is formed circumferentially on the surface of each monofilament.

10 Claims, 2 Drawing Sheets

MATTED (DELUSTERED) ARTIFICIAL HAIR AND METHOD OF PREPARATION THEREOF

This is a division of application Ser. No. 183,224 filed Apr. 19, 1988, now U.S. Pat. No. 4,880,428.

BACKGROUND OF THE INVENTION

1. Field of the Invention

The present invention relates to artificial hair such as that used to dolls, wigs, hairpieces, or an artificial hair for direct prosthetic implantation into a human body, and more particularly, to matted (delustered) artificial hair having an appearance and gloss extremely similar to that of natural human hair, and a process for producing the same.

2. Description of the Prior Art

Polyamide, polyvinyl chloride, polypropylene, polyacrylic and polyester fibers are commonly used as materials for artificial and prosthetic hairs by either melt-spinning or wet-spinning methods, for example in dolls, wigs and hairpieces, or artificial hairs used for direct prosthetic implantation into human skin.

However, the fibers used as artificial hairs require certain characteristics, i.e., features peculiar to hair, such as color, strength, weathering resistance, as well as curling property, combing property, gloss peculiar to human hair, and the like.

Particularly as to gloss, man-made fibers generally have a brilliance similar to that of glass and hence, the direct use of these as artificial hair gives the immediate impression of an artificial substitute. Especially, under sunlight or spotlights, man-made fibers glisten dazzlingly with an unnatural gloss widely different from that of natural human hair. Therefore, many efforts have been made to produce a gloss similar to that of natural human hair, and this has usually been done by providing an unevenness on the surface of the fiber, or by incorporating a delustering (matting) agent into the fiber.

For example, there has been proposed a method for improving moisture absorption and gloss by spinning and fiberizing a mixture resulting from previous incorporation of an additive extractable with a solvent into a synthetic resin composition having a fiber-forming ability, and then extracting the additive with a solvent to form a large number of small voids in the surface of the resulting fiber (see Japanese Patent Publication No. 37649/72).

However, filaments produced by this method have a significantly reduced tensile strength because of the small voids formed in the surfaces thereof. Particularly, any diameter of the small void exceeding a required range will result in a failure to provide a satisfactory gloss and also in a considerably reduced strength. Therefore, such a fiber is not fit for use as an artificial hair. In addition, any length of the small void exceeding a required range will result in a considerably degraded appearance for an artificial hair. Moreover, the sizes of the small voids largely vary depending upon proportion of additive mixed, stretching condition, additive extracting condition and the like and hence, the control thereof is difficult, leading to a low yield and a low practical value. Further, from a medical viewpoint, the fiber having the additive and solvent remaining therein cannot be used as artificial hair for direct prosthetic implantation into the human skin, because such additives and solvents are toxic to the human body.

There has also been proposed a method for providing a gloss simulating that of the human hair by incorporating an inorganic delustering agent into a synthetic resin composition, and fiberizing the mixture to increase the coarseness in surface of the fiber, thereby moderating the gloss (see Japanese Patent Publication No. 46004/72 and Japanese Patent Application Laid-open No. 57116/74). However, an artificial hair produced by this method has disadvantages in that the tensile strength of the fiber itself is substantially reduced due to the flake-like crystalline inorganic delustering agent, and the combing property is degraded due to the delustering agent projecting from the filament surface. Further, the fiber produced by this method also cannot be used as an artificial hair for direct implantation into the human skin, because the additives and solvents remaining in the fiber are toxic to the human body.

In the course of researches for developing matted (delustered) artificial hairs, the present inventors have found a method for matting the fiber by providing a large number of lightly scrubbed scratches on the surface of monofilaments in the longitudinal direction of the fiber. This method can be easily carried out by putting a bundle of fibers between fabrics or sponges impregnated with an abrasive and then withdrawing the fiber bundle under light pressure in the longitudinal direction of the fiber. However, artificial hair produced using this method had certain disadvantages in that its appearance is still clearly different from natural human hair luster and if this artificial hair is curved somewhat by hand in a bundle, the resulting bent portion glistens extremely brightly and unnaturally, and particularly glistens dazzlingly under incandescent light or the direct rays of the sun and hence, this hair can be recognized as artificial on sight.

SUMMARY OF THE INVENTION

The present invention has been accomplished to overcome the above disadvantages, and it is an object of the present invention to provide a matted (delustered) artificial hair having an appearance and gloss extremely closely resembling those of natural human hair.

It is another object of the present invention to provide a process for extremely easily and inexpensively producing such matted (delustered) artificial hair having an appearance and gloss extremely resembled to those of natural human hair.

To attain the above objects, according to a first aspect of the present invention, there is provided an artificial hair having an almost identical gloss to that of natural human hair by providing a large number of circumferential scrubbed scratches or flaws having irregular size and shape on the surface of monofilament made of a synthetic resin and having a substantially circular section.

In particular, when said large number of circumferential scrubbed scratches or flaws is formed at an angle in a range of 45° to 90° with respect to the longitudinal axis of the monofilament, it is able to provide an artificial hair having a surface appearance resembled closely to naturally occurring cuticles on the surface of human hair, whereby, it is obtained an artificial hair having surface properties and gloss extremely closely resembling those of natural human hair. If a locus of the scrubbed flaw is formed at 90°, i.e., a right angle to the longitudinal axis of the monofilament, the resulting hair is preferred, because it exhibits a gloss most similar to that of natural human hair. However, even if the direction of the flaws is inclined somewhat, the resulting artificial hair can be satisfactorily put to practical use, because any adverse affect is less revealed if that inclined angle is small. However, when any angle provided by a locus of scrubbed flaw and longitudinal axis of the monofilament becomes smaller than 45°, it is not desirable, because such an angle intensifies the disadvantage associated with the prior art method in which the scrubbed flaws are provided in the longitudinal direction of the monofilament, i.e., the disadvantage that the bent point of such artificial hair, when curved, glistens dazzlingly under bright light.

Moreover, it is most preferable to provide such that all scrubbed flaws on the surface of the monofilament consist of circumferential ones, but, in the actual manufacturing process, besides the circumferential scrubbed flaws, a lot of irregular scrubbed flaws each having a locus of irregular direction other than the circumferential direction are formed on the surface of the monofilament by the irregular movement Of abrasive grains.

However in the scrubbed flaws having loci of irregular directions other than the circumferential direction, size and depth of these are generally smaller than those of the circumferential scrubbed flaws. Thus, the existence of these scrubbed flaws having loci of irregular directions never obstructs the overall effect of the present invention i.e., providing a gloss and surface appearance resembled closely to those of natural human hair whenever the circumferential scrubbed flaws exist as the main constituents on the surface of the monofilament.

In addition, according to a second aspect of the present invention, there is provided a method of preparation of a matted (delustered) artificial hair, comprising the steps of placing a bundle of filaments of synthetic fibers which have a substantially circular section between two abrasive-coated plates, and allowing the two abrasive-coated plates to reciprocate in the opposite directions at an angle of 45° to 90° with respect to the longitudinal direction of the fiber while applying a slight pressure in the presence of an abrasive, whereby a large number of irregular scrubbed flaws is formed on the entire peripheral surface of each monofilament in the circumferential direction of the monofilament.

For a soft layer provided on the surface of the abrasive-coated plate used in the present process, a soft fabric, a leather, a rubber sheet, sponge, etc., may be employed, but a high resilient sponge made of a synthetic resin and having small cells is particularly preferred. In addition, powdery abrasive grains having grain sizes of 300 to 5,000 mesh, preferably 800 to 3,000 mesh can be used as the abrasive. In this case, an abrasion may be carried out by previously applying a powdery abrasive onto a fiber bundle and then placing the fiber bundle between the two abrasive-coated plates. In addition, the powdery abrasive may be supplied through a suitable pipe during abrasion. It is also possible to use a pasty abrasive comprising an abrasive grain of a grain size of 300 to 5,000 mesh, preferably 800 to 3,000 mesh added into a viscous liquid. The pasty abrasive is liable to be difficult to apply uniformly onto the fiber and hence, it is convenient to select a pasty abrasive having a low viscosity.

Further, it is possible to use a liquid abrasive comprising an abrasive grain of a grain size of 300 to 5,000 mesh, preferably 800 to 3,000 mesh dispersed into a liquid. In this case, the use of an aqueous solution containing a dispersant and a surfactant is most preferred, because even a small amount of such an abrasive can be uniformly distributed over the entire fiber bundle, and scrubbed flaws can be formed over all surfaces of the fibers.

With a monofilament artificial hair provided in the above manner, the scrubbed flaws formed on the surface thereof have a maximum depth of 20 $\mu$m or less and an average depth of 0.1 to 10 $\mu$m. This artificial hair cannot glisten dazzlingly under an incandescent light or the sunlight even if the fiber bundle is manually bent, and this hair has a gloss which is substantially identical to that of natural human hair. If the maximum depth of the scrubbed flaw is of 20 $\mu$m or less, then there is little influence exerted on the strength of the filament, and the tensile strength for the artificial hair and the fatigue strength in a folding test can be maintained sufficiently to put the artificial hair to practical use, while there is no adverse affect exerted upon the combing property.

Further, the presence of the aforesaid large number of scrubbed flaws provides moisture absorption capacity and imparts a softness to the hair, producing the effect of easy spreading of such as hair dressing and a feel much like natural human hair.

DESCRIPTION OF THE PREFERRED EMBODIMENTS

Figure 1:
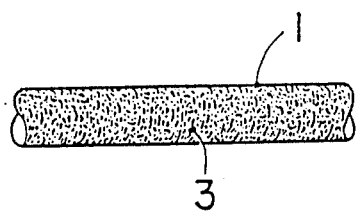
FIG. 1 is a perspective view of a matted (delustered) hair as produced by the present invention.
Figure 2:
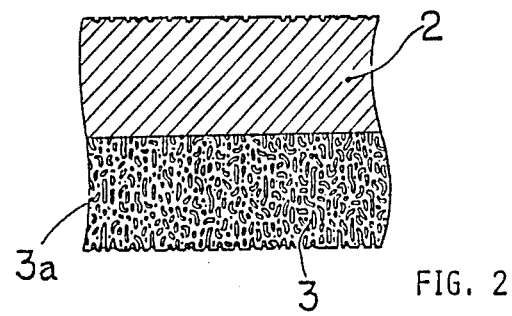
FIG. 2 is an enlarged sectional view of a part of the artificial hair shown in FIG. 1.

Referring to FIGS. 1 and 2, there is shown an artificial hair according to one embodiment of the present invention. The artificial hair 1 is a fiber which is produced by spinning of a synthetic resin such as polyamide, polyvinyl chloride, polypropylene, polyacrylic and polyester resins and which has a large number of scrubbed scratches or flaws 3 formed circumferentially with irregular size and shape at near right angles with respect to the longitudinal direction of the fiber over the entire surface of a monofilament 2 thereof having a diameter of 60 to 110 $\mu$m.

In addition, there are many small scrubbed flaws 3a having loci of irregular directions among the scrubbed flaws 3. If the maximum depth of the scrubbed flaws is larger than 20 $\mu$m, the filament has an extremely reduced strength and is liable to be cut due to the flaws and hence, the maximum depth should be controlled at 20 $\mu$m or less. In addition, if the scrubbed flaw is too small, the delustering effect is reduced, resulting in a failure to accomplish the intended object. Therefore, it is preferred to set the average depth in a range of 0.1 to 10 $\mu$m.

It is to be noted that the filament forming the artificial hair of the present invention is most normally shaped to have a truly circular section, as shown in FIG. 1, but may be shaped to have an elliptic section as well.

However, a filament having an odd-shaped section such as a star-shaped or non-uniform shaped section is not preferred, because not only is formation into such a shape by the method of the present invention difficult, but also the resulting artificial hair, when it is bent, glistens extremely brightly and unnaturally at its bent portion, as is the case with the above-described artificial hair previously developed by the present inventors and having scrubbed flaws formed on the surface thereof in the longitudinal direction of the fiber.

Embodiments of an apparatus for producing an artificial hair of the type described above in the second aspect of the present invention will now be described with reference to FIGS. 3 to 5.

Figure 3:
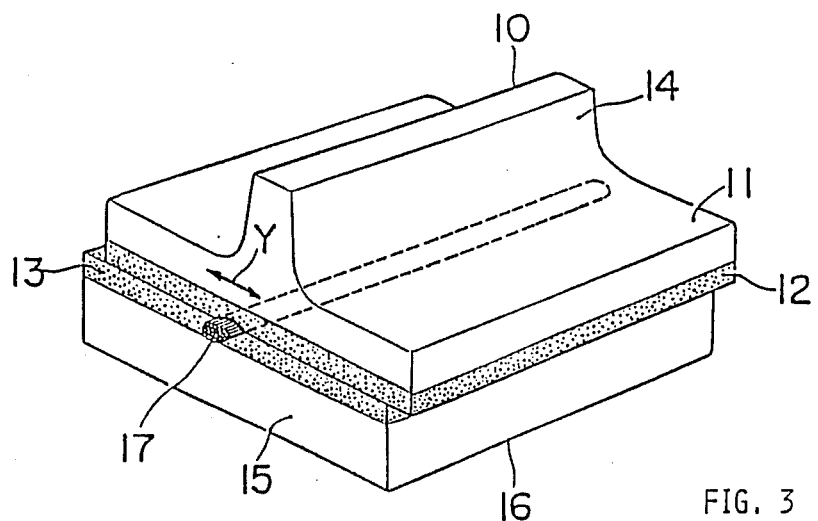
FIG. 3 is a perspective view of a manual-type apparatus for producing matted (delustered) artificial hair according to the present invention.
Figure 4:
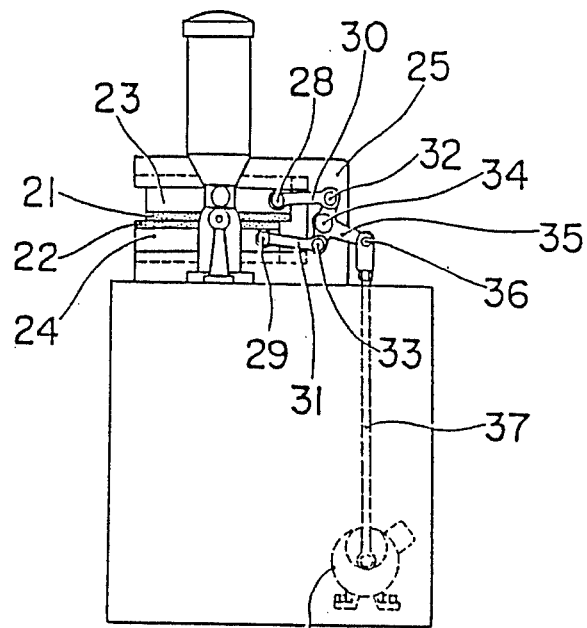
FIG. 4 is a front view of a motorized-type apparatus similar to the apparatus shown in FIG. 3.
Figure 5:
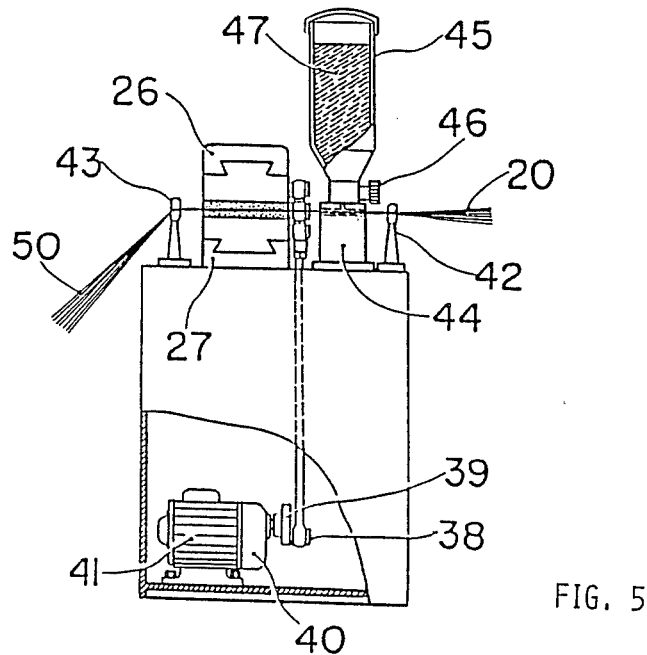
FIG. 5 is a side view of the apparatus shown in FIG. 4.

FIG. 3 illustrates an embodiment using a manual abrading tool, and FIGS. 4 and 5 illustrate an embodiment using an automatic motorized abrading machine for continuously producing a matted (delustered) artificial hair.

Referring first to FIG. 3, there is provided an abrading block 10 having a sponge 12 affixed on the underside of an upper plate 11 having a grip 14, and a base plate 16 having a sponge 13 affixed on a lower plate 15. A bundle 17 of filaments (of the number of 500 to 1,000) is placed onto the sponge 13 on the lower plate 15, and approximately 15g of a liquid abrasive comprising about 500 g of an abrasive grain of 800 to 3,000 mesh dispersed into a little water containing a dispersant and a surfactant added thereto is poured onto the fiber bundle 17. Then, the abrading block 10 is placed thereon and allowed to reciprocate in a direction Y perpendicular to the longitudinal direction of the fiber while being pressed with a slight force by hand. A stroke of reciprocation of the abrading block 10 is of about 10 mm. Approximately 100 reciprocations are continued. Thereafter, the resulting fiber is removed; washed with water and dried to give a matted (delustered) artificial hair.

The scrubbed flaws formed on the surface of the artificial hair produced in the process of the present invention have a maximum depth of 2 $\mu$m and an average depth of 1 $\mu$m.

Description will now be made of a motorized apparatus for continuously and automatically producing matted (delustered) artificial hair of the present invention.

FIG. 4 is a front view of the apparatus, and FIG. 5 is a side view of the apparatus.

Referring to FIG. 4, an upper shoe 23 having an upper sponge 21 affixed on the lower surface thereof and a lower shoe 24 having a lower sponge 22 affixed on the upper surface thereof are horizontally positioned in an opposed relation and mounted on a shoe guide 25. The upper shoe 23 is slidably mounted on an upper shoe guide 26, while the lower shoe 24 is slidably mounted on a lower shoe guide 27. An upper shoe drive rod 30 is connected at one end thereof to one end of the upper shoe 23 by an upper shoe drive pin 28. On the other hand, a lower shoe drive rod 31 is connected at one end thereof to one end of the lower shoe 24 by a lower shoe drive pin 29. The other ends of the upper and lower shoe drive rods 30 and 31 are rotatably mounted on arms of a T-shaped arm member 35 through upper and lower pins 32 and 33, respectively. The T-shaped arm member 35 is rotatably attached by pin 34. A connecting rod 37 is rotatably mounted at one end thereof to a leading end of another arm of the T-shaped arm member 35 by a drive pin 36. The other end of the connecting rod 37 is rotatably carried on a connecting rod 38 of an eccentric crank 39 which is attached to a motor 41 through a speed reducing device 40.

In FIG. 5, the reference numeral 42 is an upstream collection guide for collecting a fiber bundle 20 continuously fed from a synthetic fiber spinning and stretching machine or spool, and the reference numeral 43 is a downstream collection guide for collecting the fiber bundle delivered from the abrading machine. A liquid abrasive 47 is contained in a tank 45 and supplied in a proper amount through a flow adjuster valve 46 onto the fiber bundle 20 passing an abrasive application gate 44.

Now, to produce matted (delustered) artificial hair in this apparatus, the fiber bundle 20 continuously fed from the synthetic fiber spinning and stretching machine or spool is collected in the upstream collection guide 42 and passed through the abrasive application gate 44. A proper amount of the liquid abrasive 47 (of 800 to 3,000 mesh) in the tank 45 is supplied through the flow adjuster valve 46 onto the fiber bundle 20 which is being passed through the abrasive application gate 44. The fiber bundle 20 with the liquid abrasive 47 applied thereto is passed between the upper sponge 21 and the lower sponge 22. During this time, the upper and lower shoes 23 and 24 are allowed to reciprocate in the opposite directions through the movement of the eccentric crank 39, the T-shaped arm member 35, the upper shoe drive rod 30 and the lower shoe drive rod 31 by rotation of the motor 41 and hence, the fiber bundle 20 positioned and lightly pressed between the upper and lower sponges 21 and 22 is rubbed by the liquid abrasive 47, so that a large number of scrubbed flaws are formed over the entire surfaces of filaments substantially perpendicularly to the longitudinal direction of the fiber (exactly, the inclined angle of the scrubbed flaw is slightly less than 90°, because the fiber is travelling). The artificial hair 50 delustered in this manner is passed through the downstream collection guide 43 and wound around a take-up spool which is not shown.

The matted (delustered) artificial hair produced in this process had a maximum depth of 2 $\mu$m and an average depth of 1 $\mu$m of the scrubbed flaws formed on the surface thereof.

In an artificial hair produced by the continuous process in this embodiment, the number of the scrubbed flaws 3a having loci of irregular directions increases compared with that produced by the manual process described in the former embodiment, but it can be employed usefully enough as an artificial hair article for direct implantation into human skin as a prothesis.

While the upper and lower shoes 23 and 24 have been slided perpendicularly to the longitudinal direction of the fiber in this embodiment, it should be understood that if the travel speed of the fiber is desired to be increased, it is preferred to mount the upper and lower shoes 23 and 24 at an inclined angle larger than 45° and smaller than 90° with respect to the longitudinal direction of the fiber. In addition, as apparent from the above description that it is possible to select any angle of the scrubbed flaws by properly changing the travel speed of the fiber and the angle of upper and lower shoes mounted.

What is claimed is:

1. A method for the preparation of a matted artificial hair, comprising
    applying an abrasive material to a bundle of monofilaments of a synthetic fiber having a substantially circular section,
    scrubbing said monofilament bundle between two abrading plates each having a soft layer on a surface thereof by reciprocating the two abrading plates in the opposite directions at an angle of 45° to 90° with respect to the longitudinal direction of travel of the monofilament bundle while applying a slight pressure in the presence of said abrasive, and controlling the rate of reciprocation of said plates relative to the rate of longitudinal travel of the monofilament bundle whereby a large number of scrubbed flaws are formed predominantly circumferentially with irregular size and shape on the surface of each monofilament of the bundle of monofilaments.

2. A method of preparation of a matted (delustered) artificial hair according to claim 1, wherein said abrasive material is a powder having grain size 300 to 5,000 mesh.

3. A method of preparation of a matted (delustered) artificial hair according to claim 1, wherein said abrasive material is in the form of pasty abrasive comprising an abrasive grain of a grain size of 300 to 5,000 mesh added into a viscous liquid.

4. A method of preparation of a matted (delustered) artificial hair according to claim 1, wherein said abrasive material is in the form of liquid abrasive comprising an abrasive grain of a grain size of 300 to 5,000 mesh dispersed into a dispersing liquid.

5. A method of preparation of a matted (delustered) artificial hair according to claim 4, wherein said dispersing liquid for said liquid abrasive is an aqueous solution containing a surfactant.

6. A method according to claim 1 wherein said reciprocating is carried out to provide said scrubbed flaws having a maximum depth of 20 micrometers and an average depth of 0.1–10 micrometers.

7. A method according to claim 1 wherein said monofilaments of a synthetic fiber are produced by spinning of a synthetic resin of polyamide, polyvinyl chloride, polypropylene, polyacrylic or polyester resin.

8. A method according to claim 1 wherein said monofilaments have a diameter of 60–110 micrometers.

9. A method according to claim 1 wherein said bundle of monofilaments comprises 500–1000 monofilaments.

10. A method for the preparation of a matted (delustered) artificial hair, comprising
applying an abrasive material to a bundle of monofilaments of a synthetic fiber having a substantially circular cross-section, and
scrubbing said bundle of monofilaments in a direction generally transverse to the axis thereof between two abrading plates each having a soft layer on a surface thereof by reciprocating said plates approximately 10 mm relative to one another while applying a slight pressure, and thereby producing a large number of scrubbed flaws extending predominantly perpendicular to the longitudinal axis of said bundle of monofilaments, said scrubbed flaws being irregular in size and shape on the surface of each monofilament of the bundle of monofilaments.

* * * * *